United States Patent [19]
Dix

[11] Patent Number: 5,749,373
[45] Date of Patent: May 12, 1998

[54] HEADBAND WITH BREAK-AWAY CORD ATTACHMENT

[75] Inventor: Dan Dix, Irvine, Calif.

[73] Assignee: Moldex-Metric, Inc., Culver City, Calif.

[21] Appl. No.: 824,473

[22] Filed: Apr. 10, 1997

[51] Int. Cl.$^6$ .................................................. A61F 11/00
[52] U.S. Cl. ........................................ 128/864; 128/866
[58] Field of Search ............................... 128/846, 864, 128/857, 858; 2/209

[56] References Cited

U.S. PATENT DOCUMENTS

| | | | |
|---|---|---|---|
| 2,670,737 | 3/1954 | Cantor | 128/864 |
| 4,314,553 | 2/1982 | Westerdal | 128/864 |
| 4,615,050 | 10/1986 | Lönnstedt | 2/209 |
| 4,936,411 | 6/1990 | Leonard | 128/864 |

Primary Examiner—Michael A. Brown
Attorney, Agent, or Firm—Charles H. Schwartz

[57] ABSTRACT

A headband ear protector apparatus with break-away cord attachment including a pair of ear protectors, a resilient headband to form a band which positions the ear protectors to lie by the opposite sides of the head of a person. The headband is formed of a combination of harder and softer materials. The harder material is formed as a main support member for the ear protectors to extend between the ear protectors and provide resilience so the ear protectors will lie by the opposite sides of the head of the person. The main support member includes at least two regions having structure to receive the softer material. The softer material is received by the regions formed with openings having a particular size. A break-away cord attachment for the headband includes a flexible cord having a hard tip at each end of the cord, with the hard tips having a size larger than the particular size of the openings in the softer material to have each tip held in an opening by pressure and friction.

16 Claims, 2 Drawing Sheets

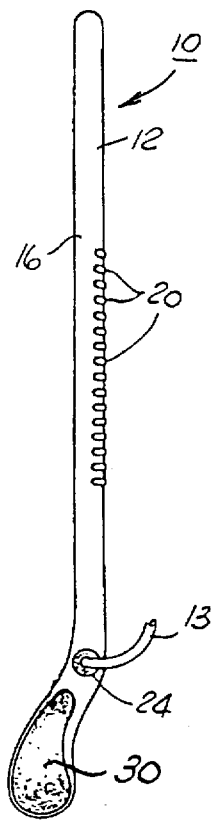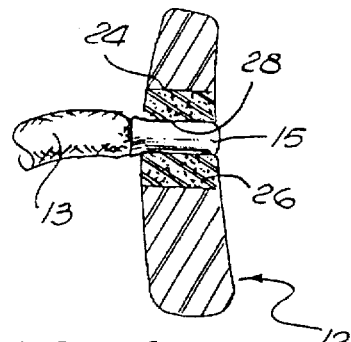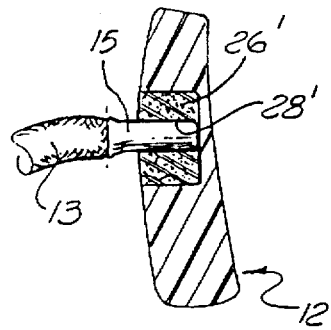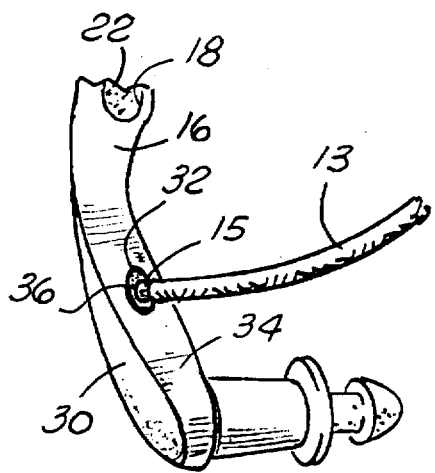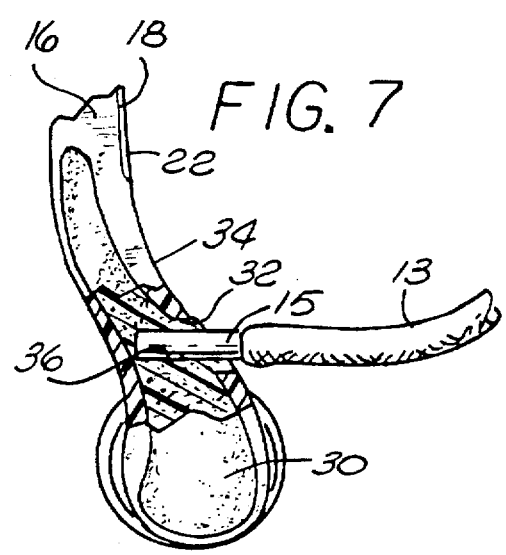

HEADBAND WITH BREAK-AWAY CORD ATTACHMENT

BACKGROUND OF THE INVENTION

The present invention relates to a headband ear protector which generally includes a headband supporting a pair of ear protectors. The headband presses the ear protectors around and partially into the outer end of the ear canal of a user. In particular, the present invention relates to a headband having a dual material construction and including a break away cord attachment.

Generally, there are a number of different types of ear protectors currently in use. One type is an earplug which is inserted fairly deeply into the ear canal. As an example, one type of such earplug is made of a slow recovery resilient foam material so that the earplug can be rolled down and inserted into the ear canal. There are times, however, when it is desired not to have an earplug inserted deeply into the ear canal.

Another type of ear protector apparatus includes a headband that presses a pair of ear protectors around and partially into the outer end of the ear canal. This type of structure avoids the necessity to insert an earplug deeply into the ear canal and is generally defined as a semi-aural headband hearing protector.

A person who would be going in and out of noisy environments would not want to wear a hearing protector all the time. They would want to be ale to fit it easily when they entered the noisy environment, and remove it just as easily when they left.

A foam earplug is not convenient for this type of use because it necessitates rolling down and inserting the plugs every time you need them. Having a headband hanging around your neck on a cord would be a very convenient feature not unlike the cords that are commonly used for holding eyeglasses.

Typically, the headband is made of a hard plastic or metal to provide for sufficient resiliency to press the ear protectors to lie against and partially into the ear canal so as to produce the desired sound attenuation. A prior application, assigned to the same assignee as the instant application is directed to the problem with this type of headband is that there is an annoying phenomena of sound transmitting through the band into the user's ear canal. This occurs most commonly when the band rubs against the user's clothing, skin whiskers or any other object. This prior application reduces significantly the sound transmission through the headband into the user's ear canal. This is accomplished by constructing the headband of two types of material: a hard plastic and a soft plastic.

As an example, the headband may have a main support member made of a hard resilient plastic. The main support member provides the resiliency so that the ear protectors can lie by and be partially inserted into the ears of the user. The hard plastic main support member includes at least one region having a structure to receive a soft plastic material. The soft plastic dampens vibrations to provide sound attenuation to reduce sound transmitted through the headband to the ear protectors.

The headband may be constructed using different methods of manufacture. These methods include co-injection molding of the type currently used to produce products such as toothbrush handles which have co-injected plastics. Other methods include molding the hard plastic main support member with the region formed as a cavity and then the soft plastic material is inserted into the cavity formed in the hard plastic support member. In either event, the headband with the dual molded material construction has the advantage of reducing the amount of sound transmitted through the band when compared with a headband that is formed only with the typical hard material.

SUMMARY OF THE INVENTION

The present invention uses a cord such as a commercial shoelace which has a very soft knitted or woven cord with relatively hard plastic tips at the ends to form a break away attachment for the headband. The hard tips provides enough stiffness to be inserted into the headband into a special hole that receives the hard tips. The hole is formed in a soft polymer material and with the size of the hole smaller than the size of the cord tip that the hole is receiving, therefore holding the hard tip by pressure and friction.

The soft polymer with the hole is formed by the same co-injection method that is described above in the pending patent application Ser. No. 08/734,201. By making this modification to the mold there is no extra cost in creating this soft polymer with the hole in the headband.

The other functional benefit of the present invention is that for safety reasons the corded band is able to pull away from the user's neck in the unlikely event that it was somehow caught in a machine or conveyor. Because the soft material flexes and the hard tip of the cord is held in only by friction, the cord releases quite easily when placed under tension.

A clearer understanding of the invention will be had with reference to the following description and drawings.

BRIEF DESCRIPTION OF THE DRAWINGS

FIG. 3 is a side view of the headband ear protector;

FIG. 4 is a cross-sectional view of one embodiment of the headband taken along lines 4—4 of FIG. 2;

FIG. 5 is a cross sectional view of a second embodiment of the invention;

FIG. 6 is a back perspective view of a third embodiment of the invention; and

FIG. 7 is a side view, partially broken away, of the third embodiment of the invention.

DETAILED DESCRIPTION OF THE PREFERRED EMBODIMENT

Figure 1:
FIG. 1 illustrates a headband ear protector apparatus constructed in accordance with the teachings of the present invention and shown positioned under the chin of a user and with the break away cord attachment positioned at the back of the neck.
Figure 2:
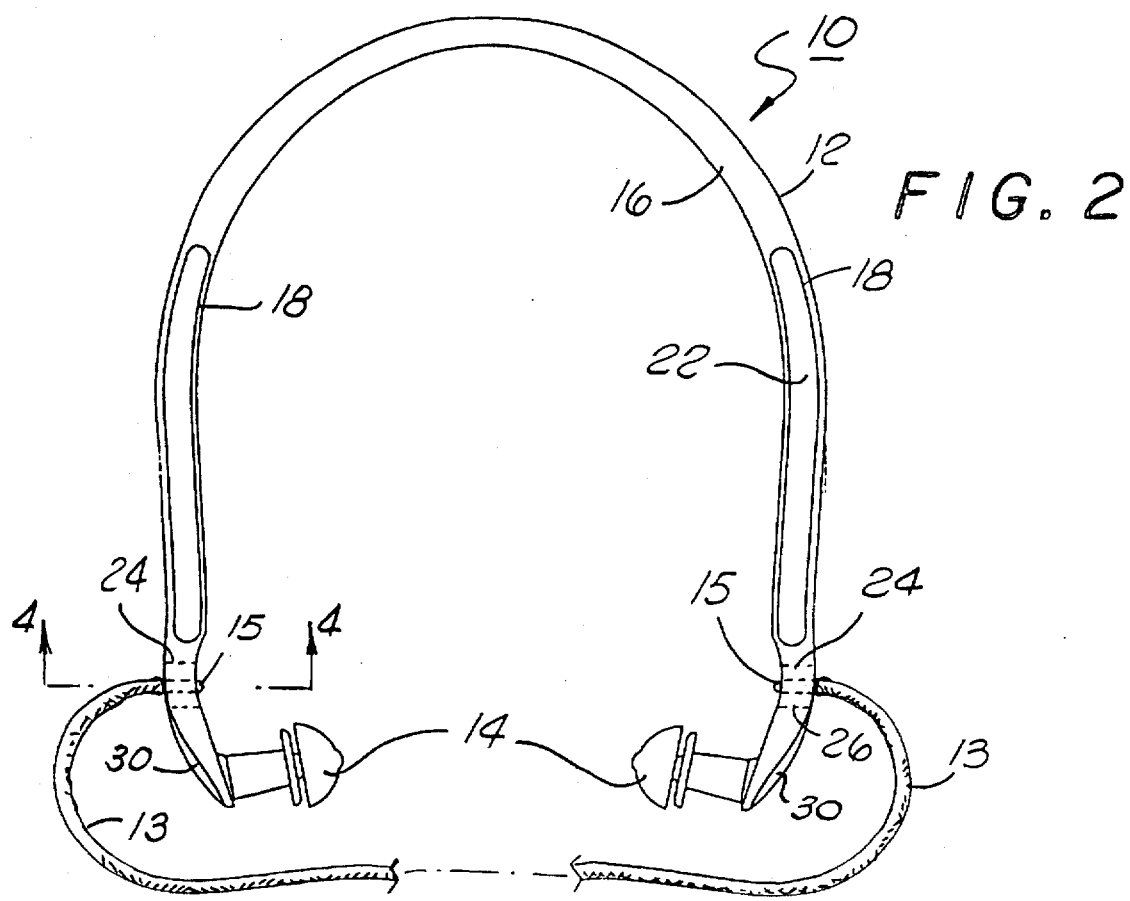
FIG. 2 is a back view of the headband ear protector.

In FIG. 1, a headband ear protector apparatus 10 of the present invention is shown and is formed by a headband 12 and ear protectors 14 and a break-away cord attachment formed by a flexible cord 13 having hard plastic tips 15 as in FIG. 2. The cord may be similar or identical to a commercial shoelace. The apparatus is shown worn under the chin of a user and with the cord 13 around the back of the neck.

Typically, the ear protectors 14 have a shape to provide for a partial insertion into the outer end of the ear canal as well as covering the outside entrance to the ear canal. The ear protectors 14 are typically made of a soft plastic material such as urethane foam, PVC foam, or silicon.

The prior application described how to significantly reduce the amount of sound transmitted through the headband by constructing the headband out of dual materials. Specifically, a hard resilient plastic material forms a main support member to maintain the ear protectors 14 positioned against the ear canal. A soft plastic material reduces the transmission of sound through the headband. As can be seen in the drawings, and specifically FIGS. 2–4, the headband 12 includes a main support member 16 constructed of a hard resilient plastic. For example, the member 16 may be polycarbonate or polypropylene as well as other hard polymers.

The main support member 16 includes at least one region having a structure to receive soft material. In the specific example shown in the drawings, two regions are formed by cavities 18 positioned at opposite ends on member 16. Each cavity extends substantially along the length of the main support member 16 along one side on both ends and with a series of smaller cavities 20 extending from within both cavities 18 through the main support member 16 to the other side.

As can be seen in FIGS. 1 through 4, each cavity 18 with the extending smaller cavities 20 within the support member 16, receive a separate soft plastic material 22. The soft plastic material 22 fills each cavity 18 and extends through the smaller cavities 20 to provide for a substantial amount of soft plastic material arranged longitudinally along and within the length of the member 16 at the areas adjacent to the ear protectors 14. The soft flexible plastic material 22 may be a flexible thermoplastic elastomer (TPE) material such as Monprene which is a trademark for a particular soft polymer sold by the QST, Incorporated. Another example of a flexible thermoplastic elastomer soft plastic may be Kraton which is a similar polymer sold by the Shell Chemical Co. and with both of these polymers specifically referred to as styrene block copolymer compounds or styrenic TPE. It is to be appreciated that other similar soft polymers may be used for the material 22.

The present invention takes advantage of the dual molding by including a pair of regions forming cavities 24 extending through the main support member 16. Soft plastic material 26 shown in FIG. 4 or 26' shown in FIG. 5 fills the cavity 24 and with the soft plastic material having an opening or hole 28 shown in FIG. 4 or 28' shown in FIG. 5. In the embodiment shown in FIG. 4, the soft plastic material 26 and opening 28 extend completely through the support member 16. in the second embodiment shown in FIG. 5, the soft plastic 26' and opening 28' extend partially within the support member 16. Each hole 28 or 28' is designed to be smaller in size than the size of the hard plastic tip 15 at each end of the cord 3. The support member 16 also includes end pods 30 of soft plastic which may form part of a third embodiment of the invention.

In the third embodiment of the invention, openings 32 are formed in edge portions 34 of the support member 16. The soft plastic, forming the pods 30, extends through the openings 32 and with holes 36 formed in the pods 30 extending through the openings 32 and with holes 36 formed in the pods 30 to receive the hard tips 15.

The headband may be constructed using one of a number of common methods. One method is a co-injection molding technique and this method is currently used to produce products such as toothbrushes. The handle of the toothbrush is constructed of a soft plastic injected into a hard plastic handle. Other techniques that may be used would be to actually mold the main hard support member first, again using injection molding techniques. After the main hard plastic member is molded then a soft plastic material may be injected into a cavity formed initially in the main support member.

As indicated above, the present invention takes a commercial shoelace or similar cord which has a very soft knitted or woven cord with relatively hard plastic tips at the ends. This tip provides enough stiffness to be inserted into the headband 12 into the special opening or hole 28 or 28'. The hole is formed in the soft polymer material 26 or 26' and is designed to be smaller in size than the hard plastic tip to thereby hold the tip 15 in the hole 28 by pressure and friction.

A main functional benefit of the present invention is that for safety reasons the corded band is able to pull away from the user's neck in the unlikely event that it was somehow caught in a machine or conveyor. Because the soft material flexes and the cord is held in only by friction, the cord releases quite easily when placed under tension.

The break-away cord attachment can be used for other safety protection products as well, including protective eyewear including safety glasses and sunglasses or even heavier products such as a conventional earmuff. In these situations a heavier gauge cord material would be used but the premise of inserting the plastic hard tip into a receiving hole in the eyewear or earmuff would be the same.

It is also to be appreciated that the cords 13 and tips 15 may take a variety of forms including that shown in the present application as well as other materials for the cord or tip. For example, the tip may be made of metal and the cord may be made of a flexible plastic.

Although the invention has been described with reference to a particular embodiment, it is to be appreciated that various adaptations and modifications may be made and the invention is only to be limited by the appended claims.

I claim:

1. A headband ear protector apparatus with break-away cord attachment including a pair of ear protectors, a resilient headband supporting, at opposite ends of the headband, the ear protectors to form a band which positions the ear protectors to lie by the opposite sides of the head of a person, the headband formed of a combination of harder and softer materials and having the following structure, the harder material formed as a main support member for the ear protectors to extend between the ear protectors and provide resilience so the ear protectors will lie by the opposite sides of the head of the person, the main support member including at least two regions having structure to receive the softer material, the softer material received by the regions formed with openings having a particular size, and a break-away cord attachment for the headband including a flexible cord having a hard tip at each end of the cord and with the hard tips having a size larger than the particular size of the openings in the softer material to have each tip held in an opening by pressure and friction.

2. The headband ear protector apparatus of claim 1 wherein the regions extend completely through the main support member so that the softer material and the tips of the cord attachments also extend through the main support member.

3. The headband ear protector apparatus of claim 1 wherein the regions extend partially through the main support member so that the softer material and the tips of the cord attachment also extend partially through the main support member.

4. The headband ear protector apparatus of claim 1 wherein two regions are formed at opposite ends of the main support member.

5. The headband ear protector apparatus of claim 1 wherein the cord attachment is formed with a hard plastic tip.

6. The headband ear protector apparatus of claim 1 wherein the cord is formed by a soft knitted or woven cord.

7. The headband of claim 1 wherein both the harder and softer materials are plastic.

8. The headband of claim 7 wherein the harder plastic may be from the following group of plastics, namely polycarbonate, polypropylene and similar hard polymers and the softer plastic may be from the following group of plastics, namely flexible thermoplastic elastomer (TPE) styrene block copolymer compound (styrenic TPE) and similar soft polymer.

9. A protective product having a main support member with break-away cord attachment to lie by the opposite sides of the head of a user, including the protective product formed of a combination of harder and softer materials and having the following structure, the harder material formed to be at least part of the main support member so the safety product can lie by the opposite sides of the head of the person, the main support member including at least two regions having structure to receive softer material, the softer material received by the regions formed with openings having a particular size, and a break-away cord attachment for the product including a flexible cord having a hard tip at each end of the cord and with the hard tips having a size larger than the particular size of the opening in the softer material to have each tip held in an opening by pressure and friction.

10. The protective product of claim 9 wherein the regions extend completely through the main support member so that the softer material and the tips of the cord also extend through the main support member.

11. The protective product of claim 9 wherein the regions extend partially through the main support member so that the softer material and the tips of the cord attachment also extend partially through the main support member.

12. The protective product of claim 9 wherein two regions are formed at opposite ends of two support members.

13. The headband of claim 9 wherein the cord attachment is formed by a soft knitted or woven cord.

14. The protective product of claim 13 wherein the hard tip of the cord attachment is formed of plastic.

15. The protective product of claim 9 wherein both the harder and softer materials are plastic.

16. The head band of claim 9 wherein the harder plastic may be from the following group of plastics, namely polycarbonate, polypropylene and similar hard polymers and the softer plastic may be from the following group of plastics, namely flexible thermoplastic elastomer (TPE), styrene block copolymer compound (styrenic TPE), and similar soft polymer.

* * * * *